(12) United States Patent
Niewöhner et al.

(10) Patent No.: US 6,930,108 B2
(45) Date of Patent: Aug. 16, 2005

(54) USE OF 2-ALKOXYPHENOL-SUBSTITUTED IMIDAZOTRIAZINONES

(75) Inventors: Ulrich Niewöhner, deceased, late of Wermelskirchen (DE); by Maria Theresia Niewöhner, legal representative, Wermelskirchen (DE); Erwin Bischoff, Wuppertal (DE); Helmut Haning, Wuppertal (DE); Afssaneh Rahbar, Erechen (DE); Tiemo-Joerg Bandel, Oberhausen (DE); Wolfgang Barth, Wuppertal (DE)

(73) Assignee: Bayer HealthCare AG, Leverkusen (DE)

(*) Notice: Subject to any disclaimer, the term of this patent is extended or adjusted under 35 U.S.C. 154(b) by 0 days.

(21) Appl. No.: 10/483,462

(22) PCT Filed: Jul. 17, 2002

(86) PCT No.: PCT/EP02/07959

§ 371 (c)(1),
(2), (4) Date: Jun. 18, 2004

(87) PCT Pub. No.: WO03/011262

PCT Pub. Date: Feb. 13, 2003

(65) Prior Publication Data

US 2004/0235838 A1 Nov. 25, 2004

(30) Foreign Application Priority Data

Jul. 23, 2001 (DE) .................................. 101 35 815

(51) Int. Cl.$^7$ .............................................. A61K 31/53
(52) U.S. Cl. ...................................................... 514/243
(58) Field of Search ......................................... 514/243

(56) References Cited

U.S. PATENT DOCUMENTS 6,362,178 B1 * 3/2002 Niewohner et al. ......... 514/218

FOREIGN PATENT DOCUMENTS

| CH | 594671 | 1/1978 |
|----|--------|--------|
| DE | 2255172 | 5/1973 |
| DE | 2364076 | 7/1974 |
| DE | 2811780 | 9/1978 |
| EP | 0009384 | 4/1980 |
| EP | 1092719 | 4/2001 |
| EP | 1097711 | 5/2001 |
| FR | 2213058 | 2/1974 |
| WO | 9428902 | 12/1994 |
| WO | 9924433 | 5/1999 |
| WO | 9967244 | 12/1999 |
| WO | 02064593 | 8/2002 |

OTHER PUBLICATIONS

Cecil Textbook of Medicine, 21$^{st}$ Ed. vol. 1, Goldman et al. (eds.), published 2000 by W.B.Saunders Co., pp 1060–1074.*

Beavo, et al., "Primary Sequence of Cyclic Nucleotide Phosphodiesterase Isozymes and the Design of Selective Inhibitors," *TIPS Reviews*, 11, 150–155 (1990).

Fawcett, et al., "Molecular Cloning and Characterization of a Distinct Human Phosphodiesterase Gene Family: PDE11A," *Proc. Nat. Acad. Sci.*, 97(7), 3702–3707 (2000).

Stoclet, et al., "Cyclic Nucleotide Phosphodiesterases as Therapeutic Targets in Cardiovascular Diseases," *Exp. Opin. Invest. Drugs*, 4(11), 1081–1100 (1995).

Masatoshi Miyahara, Isoenzymes of cyclic nucleotide phosphodiesterase in the human aorta: Characterization and the effects of E4021, European Journal of Pharmacology 384 (1995) 25–33.

* cited by examiner

*Primary Examiner*—Raymond J. Henley, III
(74) *Attorney, Agent, or Firm*—Susan M. Pellegrino

(57) ABSTRACT

The present invention relates to the use of known 2-phenyl-substituted imidazotriazinones having short, unbranched alkyl radicals in the 9-position and cGMP PDE-inhibitory properties for the production of medicaments for the treatment of cardiac insufficiency, psoriasis, female infertility, cancer, diabetes, ophthalmic disorders such as glaucoma, disorders of gastric motility, cystic fibrosis, premature labour, pulmonary hypertension, bladder disorders, prostate hyperplasia, nitrate-induced tolerance, pre-eclampsia, alopecia, Parkinson's disease, pain, tinnitus or the renal syndrome.

3 Claims, No Drawings

USE OF 2-ALKOXYPHENOL-SUBSTITUTED IMIDAZOTRIAZINONES

The present invention relates to the use of 2-alkoxyphenyl-substituted imidazotriazinones for the production of medicaments for the treatment of cardiac insufficiency, psoriasis, female infertility, cancer, diabetes, ophthalmic disorders such as glaucoma, disorders of gastric motility, cystic fibrosis, premature labour, pulmonary hypertension, bladder disorders, prostate hyperplasia, nitrate-induced tolerance, pre-eclampsia, alopecia, Parkinson's disease, pain, tinnitus or the renal syndrome.

Offenlegungsschrift DE 28 11 780 describes imidazotriazinones as bronchodilators having spasmolytic activity and inhibitory activity against cyclic adenosine monophosphate metabolizing-phosphodiesterases (cAMP PDEs, nomenclature according to Beavo: PDE-III and PDE-IV). An inhibitory action against cyclic guanosine monophosphate-metabolizing phosphodiesterases (cGMP PDEs, nomenclature according to Beavo and Reifsnyder (Trends in Pharmacol. Sci. 11, 150–155, 1990) PDE-I, PDE-II and PDE-V) is not described. No compounds are claimed which contain a sulphonamide group in the aryl radical in the 2-position. Furthermore, FR 22 13 058, CH 59 46 71, DE 22 55 172, DE 23 64 076 and EP 000 9384 describe imidazotriazinones which have no substituted aryl radical in the 2-position, and are likewise described as bronchodilators having cAMP PDE-inhibitory action.

WO 94/28902 describes pyrazolopyrimidinones which are suitable for the treatment of impotence.

WO 99/24433 and WO 99/67244 describe imidazotriazinones which are suitable for the treatment of impotence.

At present, 11 phosphodiesterases having differing specificity against the cyclic nucleotides cAMP and cGMP are described in the literature (cf. Fawcett et al., Proc. Nat. Acad. Sci. 97(7), 3072–3077 (2000). Cyclic guanosine 3',5'-monophosphate-metabolizing phosphodiesterases (cGMP PDEs) are PDE-1, 2, 5, 6, 9, 10, 11. The compounds according to the invention are potent inhibitors of phosphodiesterase 5. The differential expression of the phosphodiesterases in various cells, tissues and organs, just like the differential subcellular location of these enzymes, make possible, in combination with the selective inhibitors according to the invention, a selective increase in the cGMP concentration in specific cells, tissues and organs and thereby make possible the addressing of various processes regulated by cGMP. This is particularly to be expected if the synthesis of cGMP is increased under certain physiological conditions. For example, during sexual stimulation by the neuronal pathway, nitrogen monoxide is released in the vessels of the corpus cavemosum and thus the synthesis of cGMP is increased. This leads to a strong dilation of the vessels which supply the corpus cavemosum with blood, and thus to erection. Inhibitors of cGMP-metabolizing PDEs should therefore be particularly suitable for the treatment of erectile dysfunction.

An increase in the cGMP concentration can lead to curative, antiaggregatory, antithrombotic, antiproliferative, antivasospastic, vasodilating, natriuretic and diuretic effects and can influence the conduction in the central nervous system and thus the memory power. It can influence the short- or long-term modulation of the vascular and cardiac inotropy, the heart rhythm and the cardiac conduction (J. C. Stoclet, T. Keravis, N. Komas and C. Lugnier, Exp. Opin. Invest. Drugs (1995), 4 (11), 1081–1100).

The present invention relates to the use of compounds of the general formula (I)

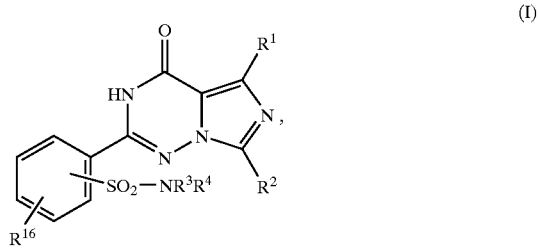

(I)

in which
R¹ represents methyl or ethyl,
R² represents ethyl or propyl,
R³ and R⁴ are identical or different and represent a straight-chain or branched alkyl chain having up to 5 carbon atoms, which is optionally up to disubstituted identically or differently by hydroxyl or methoxy,
or
R³ and R⁴ together with the nitrogen atom form a piperidinyl ring, morpholinyl ring, thiomorpholinyl ring or a radical of the formula

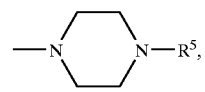

in which
R⁵ denotes hydrogen, formyl, acyl or alkoxycarbonyl in each case having up to 3 carbon atoms,
or denotes straight-chain or branched alkyl having up to 3 carbon atoms, which is optionally mono- to disubstituted, identically or differently, by hydroxyl, carboxyl, straight-chain or branched alkoxy or alkoxycarbonyl in each case having up to 3 carbon atoms or by groups of the formula —(D)$_a$-NR⁶R⁷ or —P(O)(OR⁸)(OR⁹),
in which
a denotes a number 0 or 1,
D denotes a group of the formula —CO,
R⁶ and R⁷ are identical or different and denote hydrogen or methyl,
R⁸ and R⁹ are identical or different and denote hydrogen, methyl or ethyl,
or
R⁵ denotes cyclopentyl,
and the heterocycles mentioned under R³ and R⁴, formed together with the nitrogen atom, are optionally mono- to disubstituted, identically or differently, optionally also geminally, by hydroxyl, formyl, carboxyl, acyl or alkoxycarbonyl in each case having up to 3 carbon atoms or groups of the formula —P(O)(OR¹⁰)(OR¹¹) or —(CO)$_b$NR¹²R¹³,
in which
R¹⁰ and R¹¹ are identical or different and denote hydrogen, methyl or ethyl,
b denotes a number 0 or 1,
and
R¹² and R¹³ are identical or different and denote hydrogen or methyl
and/or the heterocycles mentioned under R³ and R⁴, formed together with the nitrogen atom, are optionally substituted by straight-chain or branched alkyl having up to 3 carbon atoms, which is optionally mono- to disubstituted, identically or differently, by hydroxyl, carboxyl or by a radical of the formula $P(O)OR^{14}OR^{15}$, in which $R^{14}$ and $R^{15}$ are identical or different and denote hydrogen, methyl or ethyl, and/or the heterocycles mentioned under $R^3$ and $R^4$, formed together with the nitrogen atom, are optionally substituted by piperidinyl or pyrrolidinyl which is linked via N, and $R^{16}$ represents ethoxy or propoxy, and their salts, hydrates and/or solvates, for the production of medicaments for the treatment of cardiac insufficiency, psoriasis, female infertility, cancer, diabetes, ophthalmic disorders such as glaucoma, disorders of gastric motility, cystic fibrosis, premature labour, pulmonary hypertension, bladder disorders, prostate hyperplasia, nitrate-induced tolerance, pre-eclampsia, alopecia, Parkinson's disease, pain, tinnitus or the renal syndrome.

The use of the following compounds is particularly preferred according to the present invention:

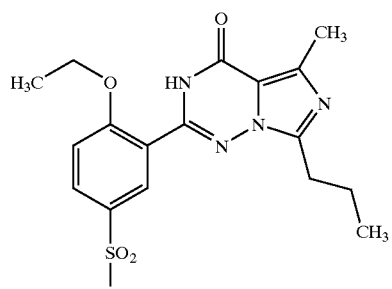
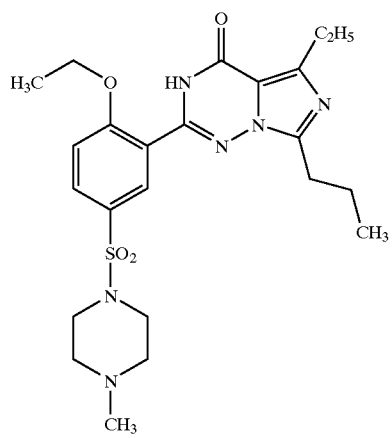
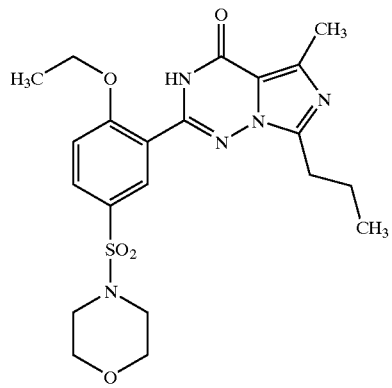
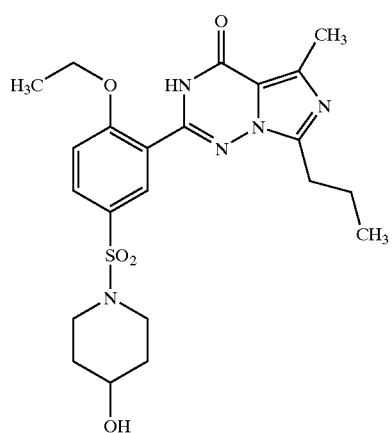
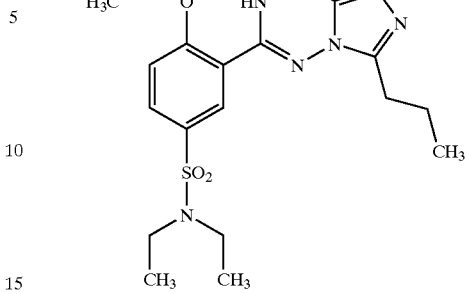
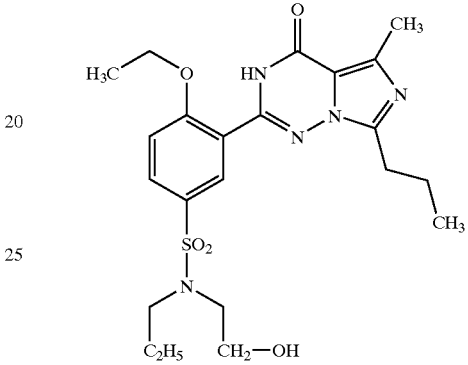

for the production of medicaments for the treatment of cardiac insufficiency, psoriasis, female infertility, cancer, diabetes, ophthalmic disorders such as glaucoma, disorders of gastric motility, cystic fibrosis, premature labour, pulmonary hypertension, bladder disorders, prostate hyperplasia, nitrate-induced tolerance, pre-eclampsia, alopecia, Parkinson's disease, pain, tinnitus or the renal syndrome.

In the context of the invention, physiologically acceptable salts are preferred. Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

Physiologically acceptable salts can likewise be metal or ammonium salts of the compounds according to the invention. Those particularly preferred are, for example, sodium, potassium, magnesium or calcium salts, and ammonium salts which are derived from ammonia or organic amines, such as, for example, ethylamine, di- or triethylamine, di- or triethanolamnine, dicyclohexylamine, dimethylaminoethanol, arginine, lysine, ethylenediamine or 2-phenylethylamine.

The compounds according to the invention, in particular the salts, can also be present as hydrates. In the context of the invention, hydrates are understood as meaning those compounds which contain water in the crystal. Such compounds can contain one or more, typically 1 to 5, equivalents of water. Hydrates can be prepared, for example, by crystallizing the compound concerned from water or a water-containing solvent.

Solvates of the compounds according to the invention are stoichiometric compositions of the compounds or their salts with solvents.

An acyl radical having 1 to 3 carbon atoms in the context of the invention represents, for example, formyl, acetyl or ethylcarbonyl.

A straight-chain or branched alkoxy radical having 1 to 3 carbon atoms in the context of the invention represents methoxy, ethoxy, n-propoxy, or isopropoxy.

An alkoxycarbonyl radical having 1 to 3 carbon atoms in the context of the invention represents methoxycarbonyl or ethoxycarbonyl.

A straight-chain or branched alkyl radical having 1 to 5 or 1 to 3 carbon atoms in the context of the invention represents, for example, methyl, ethyl, n-propyl, isopropyl, tert-butyl, n-pentyl. Straight-chain or branched alkyl radicals having 1 to 4 or 1 to 3 carbon atoms are preferred.

Halogen in the context of the invention in general represents fluorine, chlorine, bromine or iodine. Fluorine, chlorine and bromine are preferred. Fluorine and chlorine are particularly preferred.

A further embodiment of the invention relates to the use according to the invention of compounds of the general formula (I), in which the radicals $R^{16}$ and —$SO_2NR^3R^4$ are in the para-position to one another on the phenyl ring and $R^1$, $R^2$, $R^3$, $R^4$ and $R^{16}$ have the meaning indicated above.

A further embodiment of the invention relates to the use according to the invention of compounds of the general formula (Ia),

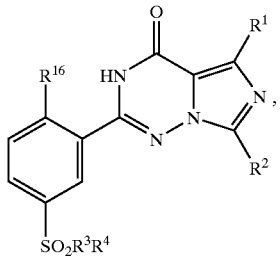

(Ia)

where $R^1$, $R^2$, $R^3$, $R^4$ and $R^{16}$ have the meaning indicated above,
and their salts, hydrates and/or solvates.

The use according to the invention of the following compounds is preferred:

2-[2-ethoxy-5-(4-methyl-piperazine-1-sulphonyl)-phenyl]-5,7-dimethyl-3H-imidazo-[5,1-f]-[1,2,4]triazin-4-one;
2-[2-ethoxy-5-(4-hydroxyethylpiperazine-1-sulphonyl)-phenyl]-5,7-dimethyl-3H-imidazo[5,1-f]-[1,2,4]triazin-4-one;
2-[2-ethoxy-5-(4-hydroxypiperidine-1-sulphonyl)-phenyl]-5,7-dimethyl-3H-imidazo-[5,1-f]-[1,2,4]triazin-4-one;
2-[2-ethoxy-5-(4-hydroxymethylpiperidine-1-sulphonyl)-phenyl]-5,7-dimethyl-3H-imidazo[5,1-f][1,2,4]triazin-4-one;
2-[2-ethoxy-5-(3-hydroxypyrrolidine-1-sulphonyl)-phenyl]-5,7-dimethyl-3H-imidazo[5,1-f]-[1,2,4]triazin-4-one;
4-ethoxy-N-ethyl-N-(2-hydroxyethyl)-3-(5,7-dimethyl-4-oxo-3,4-dihydro-imidazo-[5,1-f]-[1,2,4]triazin-2-yl)benzenesulphonamide;
N,N-diethyl-4-ethoxy-3-(5,7-dimethyl-4-oxo-3,4-dihydroimidazo[5,1-f][1,2,4]-triazin-2-yl)-benzenesulphonamide;
2-[2-ethoxy-5-(4-(2-pyrimidinyl)-piperazine-1-sulphonyl)-phenyl]-5,7-dimethyl-3H-imidazo-[5,1-f][1,2,4]triazin-4-one;
2-[2-ethoxy-5-(morpholin-4-sulphonyl)-phenyl]-5,7-dimethyl-3H-imidazo[5,1-f]-[1,2,4]triazin-4-one;
2-[2-ethoxy-5-(1,4-dioxa-6-azaspiro[4.4]nonane-6-sulphonyl)-phenyl]-5,7-dimethyl-3H-imidazo[5,1-f][1,2,4]triazin-4-one;
N,N-bis-(2-methoxyethyl)-4-ethoxy-3-(5,7-dimethyl-4-oxo-3,4-dihydroimidazo[5,1-f]-[1,2,4]triazin-2-yl)-benzenesulphonamide;
N-(3-isoxazolyl)-4-ethoxy-3-(5,7-dimethyl-4-oxo-3,4-dihydroimidazo[5,1-f][1,2,4]-triazin-2-yl)-benzenesulphonamide;
2-[2-ethoxy-5-(2-t-butoxycarbonylaminomethylmorpholine-4-sulphonyl)-phenyl]-5,7-dimethyl-3H-imidazo[5,1-f][1,2,4]triazin-4-one;
2-[2-ethoxy-5-(4-phenylpiperazine-1-sulphonyl)-phenyl]-5,7-dimethyl-3H-imidazo-[5,1-f]-[1,2,4]triazin-4-one;
2-[2-ethoxy-5-(3-hydroxy-3-methoxymethylpyrrolidine-1-sulphonyl)-phenyl]-5,7-di-methyl-3H-imidazo[5,1-f][1,2,4]triazin-4-one;
2-[2-ethoxy-5-(4-methyl-piperazine-1-sulphonyl)-phenyl]-5-methyl-7-propyl-3H-imidazo[5,1-f][1,2,4]triazin-4-one;
2-[2-ethoxy-5-(4-methyl-piperazine-1-sulphonyl)-phenyl]-5-methyl-7-propyl-3H-imidazo[5,1-f][1,2,4]triazin-4-one lactate;
2-[2-ethoxy-5-(4-methyl-piperazine-1-sulphonyl)-phenyl]-5-methyl-7-propyl-3H-imidazo[5,1-f][1,2,4]triazin-4-one hydrochloride;
2-[2-ethoxy-5-(4-ethyl-piperazine-1-sulphonyl)-phenyl]-5-methyl-7-propyl-3H-imidazo[5,1-f][1,2,4]triazin-4-one;
2-[2-ethoxy-5-(4-ethyl-piperazine-1-sulphonyl)-phenyl]-5-methyl-7-propyl-3H-imidazo[5,1-f][1,2,4]triazin-4-one hydrochloride;
2-[2-ethoxy-5-(4-methyl-1-amino-piperazine-1-sulphonyl)-phenyl]-5-methyl-7-propyl-3H-imidazo[5,1-f][1,2,4]triazin-4-one;
2-[2-ethoxy-5-(4-hydroxyethyl-1-amino-piperazine-1-sulphonyl)-phenyl]-5-methyl-7-propyl-3H-imidazo[5,1-f][1,2,4]triazin-4-one;
N,N-bishydroxyethylaminoethyl-4-ethoxy-3-(5-methyl-4-oxo-7-propyl-3,4-dihydro-imidazo[5,1-f][1,2,4]triazin-2-yl)benzenesulphonamide;
2-[2-ethoxy-5-(4-dimethoxyphosphorylmethyl-piperazine-1-sulphonyl)-phenyl]-5-methyl-7-propyl-3H-imidazo[5,1-f][1,2,4]triazin-4-one;
2-[2-ethoxy-5-(4-diethoxyphosphorylmethyl-piperidine-1-sulphonyl)-phenyl]-5-methyl-7-propyl-3H-imidazo[5,1-f][1,2,4]triazin-4-one;
2-[2-ethoxy-5-(4-hydroxy-piperidine-1-sulphonyl)-phenyl]-5-methyl-7-propyl-3H-imidazo[5,1-f][1,2,4]triazin-4-one;

2-{2-ethoxy-5-[4-(2-hydroxy-ethyl)-piperazine-1-sulphonyl]-phenyl}-5-methyl-7-propyl-3H-imidazo[5,1-f][1,2,4]triazin-4-one;

2-{2-ethoxy-5-[4-(2-hydroxy-ethyl)-piperazine-1-sulphonyl]-phenyl}-5-methyl-7-propyl-3H-imidazo[5,1-f][1,2,4]triazin-4-one hydrochloride;

2-{2-ethoxy-5-[4-(3-hydroxy-propyl)-piperazine-1-sulphonyl]-phenyl}-5-methyl-7-propyl-3H-imidazo[5,1-f][1,2,4]triazin-4-one;

N-allyl-4-ethoxy-N-(2-hydroxy-ethyl)-3-(5-methyl-4-oxo-7-propyl-3,4-dihydro-imidazo[5,1-f][1,2,4]triazin-2-yl)benzenesulphonamide;

N-ethyl-4-ethoxy-N-(2-hydroxy-ethyl)-3-(5-methyl-4-oxo-7-propyl-3,4-dihydro-imidazo[5,1-f][1,2,4]triazin-2-yl)benzenesulphonamide;

N,N-diethyl-4-ethoxy-3-(5-methyl-4-oxo-7-propyl-3,4-dihydro-imidazo[5,1-f][1,2,4]triazin-2-yl)benzenesulphonamide;

N-(2-methoxyethyl)-3-(5-methyl-4-oxo-7-propyl-3,4-dihydro-imidazo[5,1-f][1,2,4]triazin-2-yl)-4-ethoxy-benzenesulphonamide;

N-(2-N,N-dimethylethyl)-3-(5-methyl-4-oxo-7-propyl-3,4-dihydro-imidazo[5,1-f][1,2,4]triazin-2-yl)-4-ethoxy-benzenesulphonamide;

N-[3-(1-morpholino)propyl]-3-(5-methyl-4-oxo-7-propyl-3,4-dihydro-imidazo [5,1-f][1,2,4]triazin-2-yl)-4-ethoxy-benzenesulphonamide;

N-{3-[1-(4-methyl)piperazino]-propyl}-3-(5-methyl-4-oxo-7-propyl-3,4-dihydro-imidazo[5,1-f][1,2,4]triazin-2-yl)-4-ethoxy-benzenesulphonamide;

2-{2-ethoxy-5-[4-(2-methoxy-ethyl)-piperazine-1-sulphonyl]-phenyl}-5-methyl-7-propyl-3H-imidazo[5,1-f][1,2,4]triazin-4-one;

2-{2-ethoxy-5-[4-(2-N,N-dimethyl-ethyl)-piperazine-1-sulphonyl]-phenyl}-5-methyl-7-propyl-3H-imidazo[5,1-f][1,2,4]triazin-4-one;

2-{2-ethoxy-5-[4-(3-N,N-dimethyl-propyl)-piperazine-1-sulphonyl]-phenyl}-5-methyl-7-propyl-3H-imidazo[5,1-f][1,2,4]triazin-4-one;

2-[2-ethoxy-5-(4-dioxolano-piperidine-1-sulphonyl)-phenyl]-5-methyl-7-propyl-3H-imidazo[5,1-f][1,2,4]triazin-4-one;

2-[2-ethoxy-5-(4-(5-methyl-4-furoxancarbonyl)-piperazine-1-sulphonyl)-phenyl]-5-methyl-7-propyl-3H-imidazo[5,1-f][1,2,4]triazin-4-one;

2-{2-ethoxy-5-[4-acetyl-piperazine-1-sulphonyl]-phenyl}-5,7-methyl-7-propyl-3H-imidazo[5,1-f][1,2,4]triazin-4-one;

2-{2-ethoxy-5-[4-formyl-piperazine-1-sulphonyl]-phenyl}-5-methyl-7-propyl-3H-imidazo[5,1-f][1,2,4]triazin-4-one;

2-[2-ethoxy-5-(3-butylsydnoneimine)-1-sulphonyl)-phenyl]-5-methyl-7-propyl-3H-imidazo[5,1-f][1,2,4]triazin-4-one;

5-methyl-2-[5-(4-methyl-piperazine-1-sulphonyl)-2-propoxy-phenyl]-7-propyl-3H-imidazo[5,1-f][1,2,4]triazin-4-one;

5-methyl-2-[5-(4-methyl-piperazine-1-sulphonyl)-2-propoxy-phenyl]-7-propyl-3H-imidazo[5,1-f][1,2,4]triazin-4-one hydrochloride;

2-[5-(4-hydroxypiperidine-1-sulphonyl)-2-propoxy-phenyl]-5-methyl-7-propyl-3H-imidazo[5,1-f][1,2,4]triazin-4-one;

2-[5-(4-hydroxymethylpiperidine-1-sulphonyl)-2-propoxy-phenyl]-5-methyl-7-propyl-3H-imidazo[5,1-f][1,2,4]triazin-4-one;

2-{5-[4-(2-hydroxyethyl)-piperazine-1-sulphonyl]-2-propoxy-phenyl}-5-methyl-7-propyl-3H-imidazo[5,1-f][1,2,4]triazin-4-one;

N-(1,1-dioxotetrahydro-1$\Delta^6$-thiophen-3-yl)-3-(5-methyl-4-oxo-7-propyl-3,4-dihydro-imidazo-[5,1-f][1,2,4]triazin-2-yl)-4-propoxy-benzenesulphonamide;

N-(2-dimethylaminoethyl)-N-methyl-3-(5-methyl-4-oxo-7-propyl-3,4-dihydro-imidazo[5,1-f][1,2,4]triazin-2-yl)-4-propoxy-benzenesulphonamide;

3-(5-methyl-4-oxo-7-propyl-3,4-dihydro-imidazo[5,1-f][1,2,4]triazin-2-yl)-N-(3-morpholin-4-yl-propyl)-4-propoxy-benzenesulphonamide;

N,N-bis-(2-hydroxyethyl)-3-(5-methyl-4-oxo-7-propyl-3,4-dihydro-imidazo[5,1-f][1,2,4]triazin-2-yl)-4-propoxy-benzenesulphonamide;

N-(3-hydroxybenzyl)-3-(5-methyl-4-oxo-7-propyl-3,4-dihydro-imidazo[5,1-f][1,2,4]triazin-2-yl)-4-propoxy-benzenesulphonamide;

N-ethyl-N-(2-hydroxyethyl)-3-(5-methyl-4-oxo-7-propyl-3,4-dihydro-imidazo[5,1-f][1,2,4]triazin-2-yl)-4-propoxy-benzenesulphonamide;

N-(3-ethoxypropyl)-3-(5-methyl-4-oxo-7-propyl-3,4-dihydro-imidazo[5,1-f]-[1,2,4]triazin-2-yl)-4-propoxy-benzenesulphonamide;

2-[5-(4-hydroxypiperidine-1-sulphonyl)-2-propoxy-phenyl]-5-methyl-7-propyl-3H-imidazo[5,1-f][1,2,4]triazin-4-one;

3-(5-methyl-4-oxo-7-propyl-3,4-dihydro-imidazo[5,1-f][1,2,4]triazin-2-yl)-4-propoxy-N-pyridin-4-yl-benzenesulphonamide;

N,N-diethyl-3-(5-methyl-4-oxo-7-propyl-3,4-dihydro-imidazo[5,1-f][1,2,4]triazin-2-yl)-4-propoxy-benzenesulphonamide;

1-[3-(5-methyl-4-oxo-7-propyl-3,4-dihydro-imidazo[5,1-f][1,2,4]triazin-2-yl)-4-propoxy-benzenesulphonyl]-piperidine-4-carboxylic acid;

5-methyl-2-[5-(morpholine-4-sulphonyl)-2-propoxy-phenyl]-7-propyl-3H-imidazo-[5,1-f][1,2,4]triazin-4-one;

N-(2-hydroxyethyl)-N-methyl-3-(5-methyl-4-oxo-7-propyl-3,4-dihydro-imidazo[5,1-f][1,2,4]triazin-2-yl)-4-propoxy-benzenesulphonamide;

N-(2-hydroxyethyl)-3-(5-methyl-4-oxo-7-propyl-3,4-dihydro-imidazo[5,1-f][1,2,4]triazin-2-yl)-4-propoxy-N-propyl-benzenesulphonamide;

N-[2-(3,4-dimethoxy-phenyl)ethyl]-N-methyl-3-(5-methyl-4-oxo-7-propyl-3,4-dihydro-imidazo[5,1-f][1,2,4]triazin-2-yl)-4-propoxy-benzenesulphonamide;

N-allyl-N-(2-hydroxyethyl)-3-(5-methyl-4-oxo-7-propyl-3,4-dihydroimidazo[5,1-f][1,2,4]triazin-2-yl)-4-propoxybenzenesulphonamide;

N-allyl-N-cyclopentyl-3-(5-methyl-4-oxo-7-propyl-3,4-dihydroimidazo[5,1-f][1,2,4]triazin-2-yl)-4-propoxybenzenesulphonamide;

N-allyl-N-ethyl-3-(5-methyl-4-oxo-7-propyl-3,4-dihydroimidazo [5,1-f][1,2,4]triazin-2-yl)-4-propoxybenzenesulphonamide;

2-[2-ethoxy-4-methoxy-5-(4-methylpiperazine-1-sulphonyl)-phenyl]-5-methyl-7-propyl-3H-imidazo [5,1-f][1,2,4]triazin-4-one;

2-{2-ethoxy-5-[4-(2-hydroxyethyl)-piperazine-1-sulphonyl]-4-methoxy-phenyl}-5-methyl-7-propyl-3H-imidazo[5,1-f][1,2,4]triazin-4-one;

4-ethoxy-N-ethyl-N-(2-hydroxyethyl)-2-methoxy-5-(5-methyl-4-oxo-7-propyl-3,4-dihydro-imidazo[5,1-f][1,2,4]triazin-2-yl)-benzenesulphonamide;

4-ethoxy-N-(4-ethoxyphenyl)-2-methoxy-5-(5-methyl-4-oxo-7-propyl-3,4-dihydro-imidazo[5,1-f][1,2,4]triazin-2-yl)-benzenesulphonamide;

4-ethoxy-N-ethyl-N-(2-hydroxy-ethyl)-3-(5-ethyl-4-oxo-7-propyl-3,4-dihydroimidazo[5,1-f][1,2,4]triazin-2-yl)benzenesulphonamide;

N-(2-methoxyethyl)-3-(5-ethyl-4-oxo-7-propyl-3,4-dihydro-imidazo[5,1-f][1,2,4]triazin-2-yl)-4-ethoxybenzenesulphonamide;

N,N-bis-(2-methoxyethyl)-3-(5-ethyl-4-oxo-7-propyl-3,4-dihydroimidazo[5,1-f][1,2,4]tri-azin-2-yl)-4-ethoxybenzenesulphonamide;

2-[5-(4-hydroxypiperidine-1-sulphonyl)-2-ethoxyphenyl]-5-ethyl-7-propyl-3H-imidazo[5,1-f]-[1,2,4]triazin-4-one;

2-[5-(4-hydroxymethylpiperidine-1-sulphonyl)-2-ethoxyphenyl]-5-ethyl-7-propyl-3H-imidazo[5,1-f](1,2,4]triazin-4-one;

2-{2-ethoxy-5-[4-(2-hydroxyethyl)-piperazine-1-sulphonyl]-phenyl}-5-ethyl-7-propyl-3H-imidazo[5,1-f][1,2,4]triazin-4-one;

2-[2-ethoxy-5-(4-methylpiperazine-1-sulphonyl)-phenyl]-5-ethyl-7-propyl-3H-imidazo[5,1-f]-[1,2,4]triazin-4-one;

2-[2-ethoxy-5-(4-methylpiperazine-1-sulphonyl)-phenyl]-5-ethyl-7-propyl-3H- imidazo[5,1-f][1,2,4]triazin-4-one hydrochloride;

3-(5-ethyl-4-oxo-7-propyl-3,4-dihydroimidazo[5,1-f][1,2,4]triazin-2-yl)-N-(3-morpholin-4-yl-propyl)-4-ethoxybenzenesulphonamide;

N-(2-hydroxyethyl)-3-(5-ethyl-4-oxo-7-propyl-3,4-dihydro-imidazo[5,1-f][1,2,4]triazin-2-yl)-4-ethoxy-N-propyl-benzenesulphonamide;

2-[2-ethoxy-5-(4-ethyl-piperazine-1-sulphonyl)-phenyl]-5-methyl-7-propyl-3H- imidazol[5,1-f][1,2,4]triazin-4-one hydrochloride trihydrate;

2-[2-ethoxy-5-(4-ethyl-piperazine-1-sulphonyl)-phenyl]-5-methyl-7-propyl-3H-imidazo[5,1-f][1,2,4]triazin-4-one dihydrochloride.

The compounds according to the invention can be prepared according to the description in WO 99/24433, reference to whose disclosure in this respect is expressly made here.

The compounds according to the invention inhibit the c-GMP-metabolizing phosphodiesterases 5. This leads to an increase in c-GMP. The differential expression of the phosphodiesterases in various cells, tissues and organs, just like the differential subcellular location of these enzymes, make possible, in combination with the selective inhibitors according to the invention, a selective addressing of the various processes regulated by cGMP.

Moreover, the compounds according to the invention reinforce the action of substances, such as, for example, EDRF (endothelium derived relaxing factor), ANP (atrial natriuretic peptide), of nitro vasodilators and all other substances which increase the cGMP concentration in a manner other than phosphodiesterase inhibitors.

The compounds of the general formula (I) according to the invention are therefore suitable for the prophylaxis and/or treatment of disorders in which an increase in the cGMP concentration is beneficial, i.e. disorders which are connected with cGMP-regulated processes (in English usually simply designated as 'cGUP-related diseases'). According to the present invention, those concerned here are cardiac insufficiency, psoriasis, female infertility, cancer, diabetes, ophthalmic disorders such as glaucoma, disorders of gastric motility, cystic fibrosis, premature labour, pulmonary hypertension, bladder disorders, prostate hyperplasia, nitrate-induced tolerance, pre-eclampsia, alopecia, Parkinson's disease, pain, tinnitus or the renal syndrome.

Temporary or permanent damage to the eyes can result on account of constriction of a blood vessel and a defective supply of the eye with nutrients resulting therefrom. For example, this—in addition to high intraocular pressure—can be one of the causes of glaucoma (cf. e.g. Van de Voorde, J. Invest. Ophthal. & Vis. Sci. 39(9):1642–1646 (1998)). There are reports about a slowing of the progress of glaucomatous optical neuropathy in the case of systemic administration of an NO donor, which could be attributed to a dilation of the blood vessels in the eye (cf. Afshari, Invest. Ophthalmol. Vis. Sci. 38(Suppl.):S277 (1997); Grunwald, British J. Ophthal. 83(2):162–167 (1999)). Inhibitors of the cGMP PDE lead—as described above—analogously to NO donors, to an increase in the cGMP level and can thus, inter alia, cause a vasodilation of the blood vessels in the eyes and thus be used for the treatment of glaucomas.

In principle, the compounds of the formula (I), however, can also be used for the treatment of other disorders of the eye, for example for the treatment or prophylaxis of central retinal or posterior ciliary arterial occlusion, central retinal venous occlusion, optical neuropathy such as anterior ischaemic optical neuropathy and glaucomatous optical neuropathy, and of macular degeneration.

The activity of the compounds of the formula (I) as inhibitors of the phosphodiesterases (PDEs) is described in WO 99/24433, reference to whose contents in this respect is expressly made.

The active compounds and their physiologically acceptable salts (e.g. hydrochlorides, maleates or lactates) can be converted in a known manner into the customary formulations, such as tablets, coated tablets, pills, granules, aerosols, syrups, emulsions, suspensions and solutions, using inert, non-toxic pharmaceutically suitable vehicles or solvents. The therapeutically active compound should in each case be present here in a concentration of approximately 0.5 to 9% by weight of the total mixture, i.e. in amounts which are sufficient in order to achieve the dosage range indicated.

The formulations are prepared, for example, by extending the active compounds using solvents and/or vehicles, optionally using emulsifying agents and/or dispersing agents, where, for example, if water is used as a diluent, organic solvents can optionally be used as auxiliary solvents.

Administration is carried out in a customary manner, preferably orally, transdermally or parenterally, e.g. perlingually, buccally, intravenously, nasally, rectally or by inhalation.

For use in man, in the case of oral administration doses of 0.001 to 50 mg/kg, preferably 0.01 mg/kg–20 mg/kg, are more usefully administered. In the case of parenteral administration, such as, for example, nasally, buccally or by inhalation via the mucous membranes, a dose of 0.001 mg/kg–0.5 mg/kg is useful.

In spite of this, it may optionally be necessary to depart from the amounts mentioned, namely depending on the body weight or on the type of administration route, on individual behaviour towards the medicament, the manner of its formulation and the time or interval at which administration takes place. Thus in some cases it may be sufficient to manage with less than the abovementioned minimum amount, while in other cases the upper limit mentioned has to be exceeded. In the case of the administration of relatively large amounts, it may be advisable to divide these into a number of individual doses over the course of the day.

The compounds according to the invention are also suitable for use in veterinary medicine. For applications in veterinary medicine, the compounds or their non-toxic salts are administered in a suitable formulation in agreement with the general veterinary medical practices. The veterinary surgeon can fix the type of administration and the dose according to the type of the animal to be treated.

What is claimed is:

1. A method for the treatment of, psoriasis, female infertility, diabetes, ophthalmic disorders, glaucoma, disorders of gastric motility, cystic fibrosis, premature labour, pulmonary hypertension, nitrate-induced tolerance, pre-eclampsia, alopecia, Parkinson's disease, pain, tinnitus or the renal syndrome comprising administering to a subject in need thereof an effective amount of one or more 2-phenyl-substituted imidazotriazinones of the general formula (I)

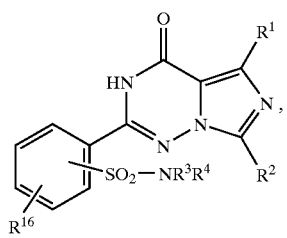

(I)

in which
R$^1$ represents methyl or ethyl,
R$^2$ represents ethyl or propyl,
R$^3$ and R$^4$ are identical or different and represent a straight-chain or branched alkyl chain having up to 5 carbon atoms, which is optionally up to disubstituted identically or differently by hydroxyl or methoxy,
or
R$^3$ and R$^4$ together with the nitrogen atom form a piperidinyl ring, morpholinyl ring, thio-morpholinyl ring or a radical of the formula

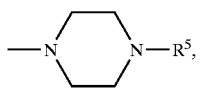

in which
R$^5$ denotes hydrogen, formyl, acyl or alkoxycarbonyl in each case having up to 3 carbon atoms,
or denotes straight-chain or branched alkyl having up to 3 carbon atoms, which is optionally mono- to disubstituted, identically or differently, by hydroxyl, carboxyl, straight-chain or branched alkoxy or alkoxycarbonyl in each case having up to 3 carbon atoms or by groups of the formula —(D)$_a$-NR$^6$R$^7$ or —P(O)(OR$^8$)(OR$^9$),
in which
a denotes a number 0 or 1,
D denotes a group of the formula —CO,
R$^6$ and R$^7$ are identical or different and denote hydrogen or methyl,
R$^8$ and R$^9$ are identical or different and denote hydrogen, methyl or ethyl,
or
R$^5$ denotes cyclopentyl,
and the heterocycles mentioned under R$^3$ and R$^4$, formed together with the nitrogen atom, are optionally mono- to disubstituted, identically or differently, optionally also geminally, by hydroxyl, formyl, carboxyl, acyl or alkoxycarbonyl in each case having up to 3 carbon atoms or groups of the formula —P(O)(OR$^{10}$)(OR$^{11}$) or —(CO)$_b$NR$^{12}$R$^{13}$,
in which
R$^{10}$ and R$^{11}$ are identical or different and denote hydrogen, methyl or ethyl, b denotes a number 0 or 1,
and
R$^{12}$ and R$^{13}$ are identical or different and denote hydrogen or methyl
and/or the heterocycles mentioned under R$^3$ and R$^4$, formed together with the nitrogen atom, are optionally substituted by straight-chain or branched alkyl having up to 3 carbon atoms, which is optionally mono- to disubstituted, identically or differently, by hydroxyl, carboxyl or by a radical of the formula P(O)OR$^{14}$OR$^{15}$,
in which
R$^{14}$ and R$^{15}$ are identical or different and denote hydrogen, methyl or ethyl,
and/or the heterocycles mentioned under R$^3$ and R$^4$, formed together with the nitrogen atom, are optionally substituted by piperidinyl or pyrrolidinyl linked via N,
and
R$^{16}$ represents ethoxy or propoxy,
and their salts, hydrates and/or solvates.

2. The method according to claim 1, wherein the compounds are of the general formula (Ia),

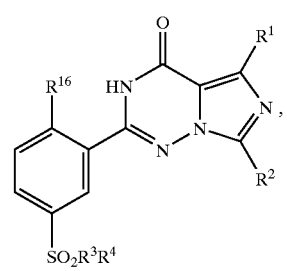

(Ia)

where R$^1$, R$^2$, R$^3$, R$^4$ and R$^{16}$ have the meaning indicated in claim 1, and their salts, hydrates and/or solvates.

3. The method according to claim 1 or 2, wherein the 2-phenyl-substituted imidazotriazinones have the following structures:

Structure

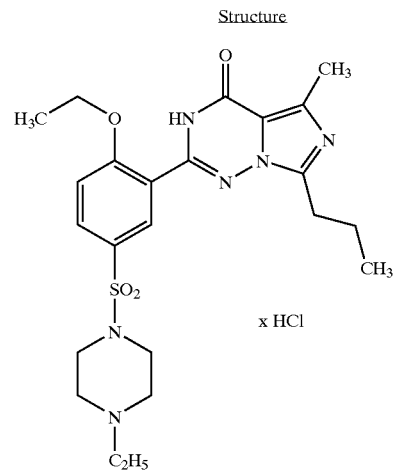

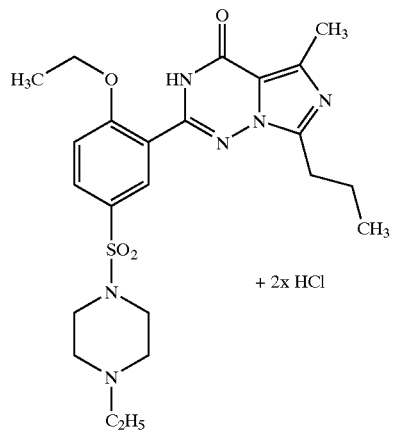
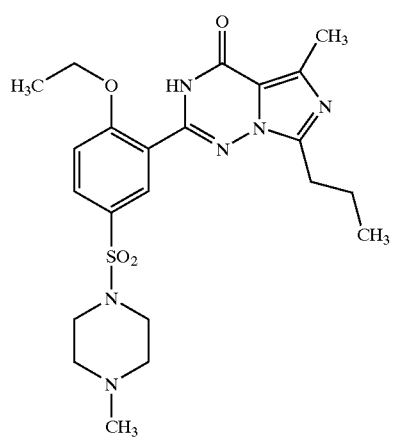
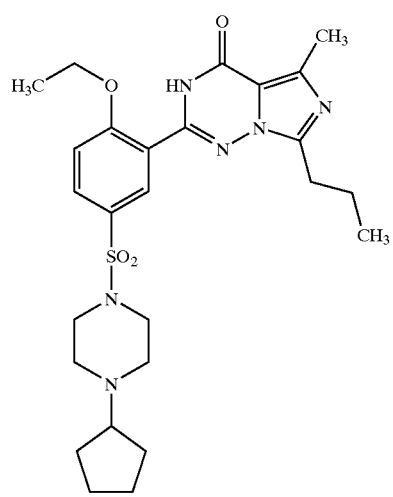
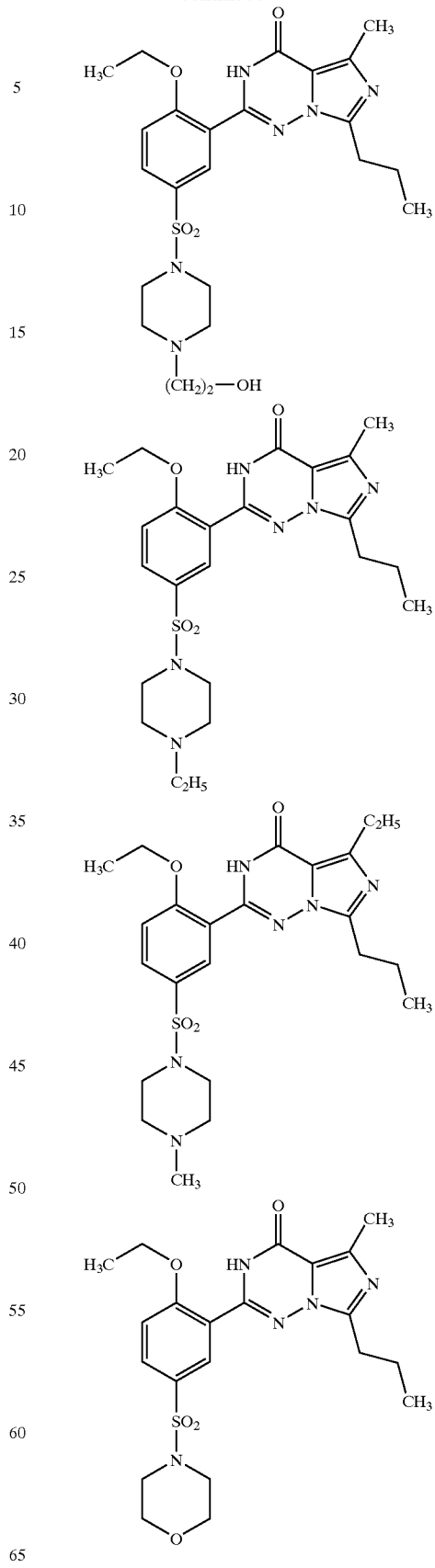

-continued
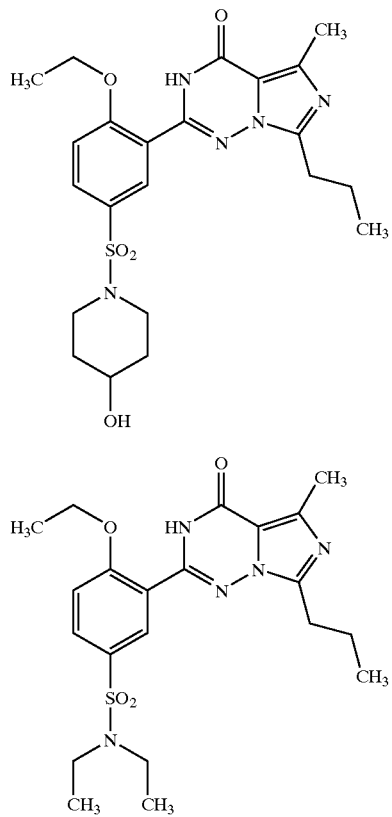
-continued
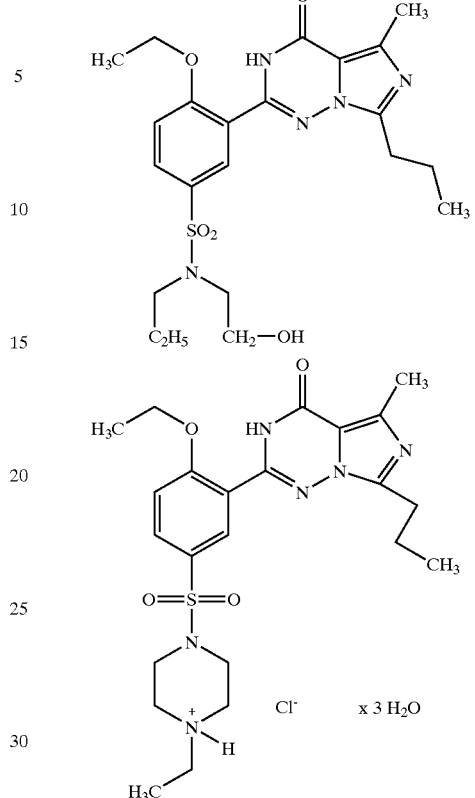
* * * * *